United States Patent [19]

Frank et al.

[11] 4,308,249

[45] Dec. 29, 1981

[54] RADIOPHARMACEUTICAL COMPLEXES OF N-(TRI-SUBSTITUTED ALKYL)-IMINODIACETIC ACIDS

[75] Inventors: Patricia Frank, Evanston; Stephen Kraychy, Northbrook; Ernest F. Le Von, Evanston, all of Ill.

[73] Assignee: G. D. Searle & Co., Chicago, Ill.

[21] Appl. No.: 102,718

[22] Filed: Dec. 13, 1979

[51] Int. Cl.$^3$ ............... A61K 49/00; A61K 43/00; G01T 1/00
[52] U.S. Cl. ................... 424/1; 260/429 J; 562/437; 562/441; 424/1.5; 424/9
[58] Field of Search ............ 424/1, 9, 1.5; 562/433, 562/437, 441; 260/429 J

[56] References Cited

U.S. PATENT DOCUMENTS

| | | | |
|---|---|---|---|
| 3,740,418 | 6/1973 | Rajamani et al. | 424/1 |
| 3,994,966 | 11/1976 | Sundberg et al. | 562/437 |
| 4,017,596 | 4/1977 | Loberg et al. | 424/1 |
| 4,088,747 | 5/1978 | Hunt et al. | 424/1 |

OTHER PUBLICATIONS

Brookeman, et al., Chemical Abstracts vol. 87, 1977, abstract #179937g.

*Primary Examiner*—Christine M. Nucker
*Attorney, Agent, or Firm*—James R. Henes; Albert Tockman; James G. Passe

[57] ABSTRACT

Complexes of radiolabelled metals with N-(tri-substituted alkyl)-iminodiacetic acids or salts thereof having utility as radiopharmaceutical agents for monitoring the activity of an organ, their preparation and a method employing such complexes for externally monitoring the activity of an organ are disclosed.

9 Claims, 3 Drawing Figures

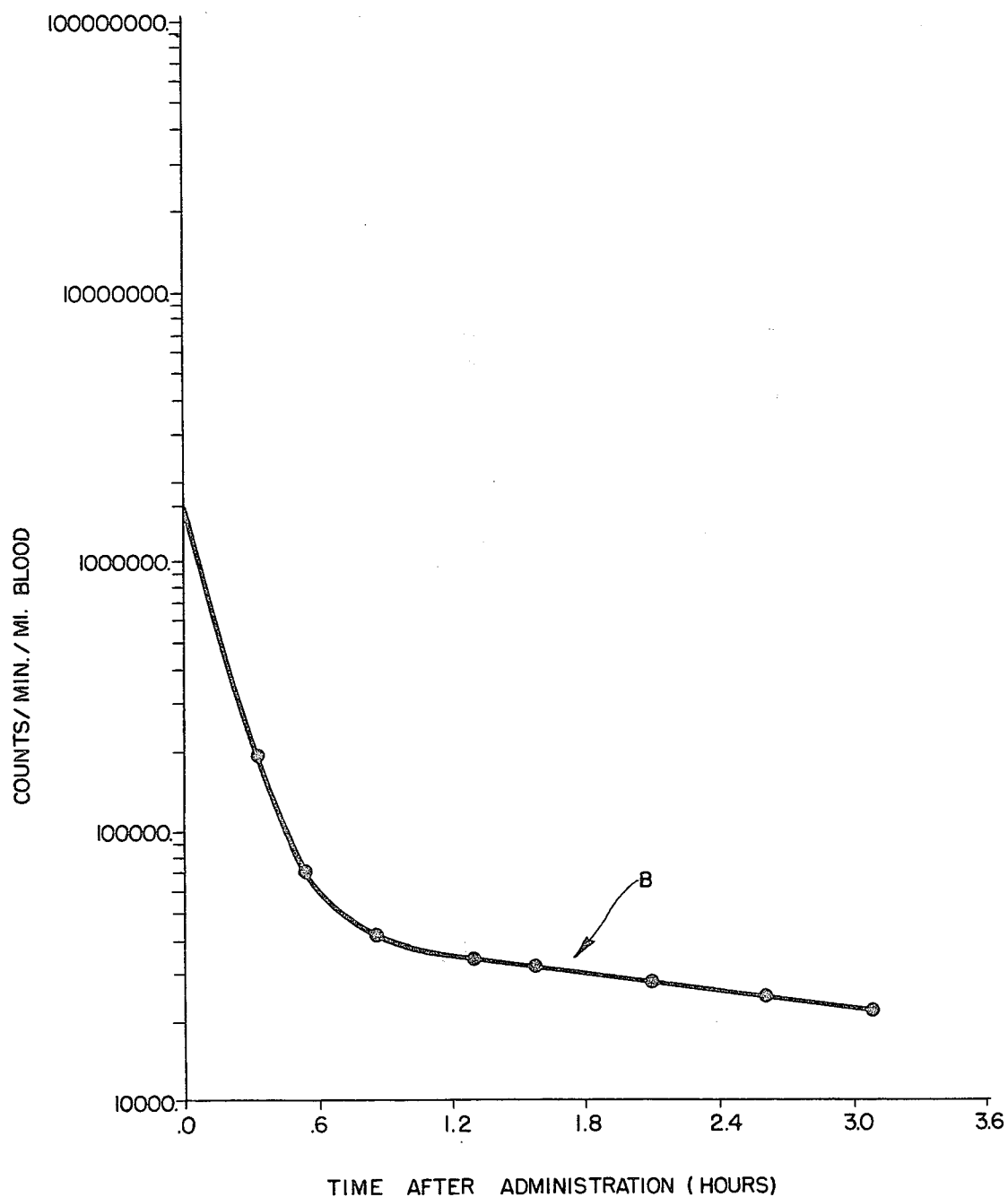

RADIOPHARMACEUTICAL COMPLEXES OF N-(TRI-SUBSTITUTED ALKYL)-IMINODIACETIC ACIDS

BACKGROUND OF THE INVENTION

1. Field of the Invention

This invention relates generally to radiopharmaceutical agents and more particularly concerns chelates of radiolabelled metals and N-(tri-substituted alkyl)-iminodiacetic acids or salts thereof which function as radiopharmaceutical liver imaging and function agents.

2. Description of the Prior Art

The rate of disappearance of an intravenously administered radiopharmaceutical agent from the plasma is related to both its distribution throughout the body and its elimination from the body. An analysis of the clearance, or rate of disappearance, of the radiopharmaceutical agent from the plasma—which can be represented by a plot of the logarithm of the experimentally measured radiopharmaceutical activity in the plasma as the ordinate versus time after administration as the abscissa—can define the number and sizes of the individual compartments of distribution of the radiopharmaceutical agent within the body. Since the clearance of the radiopharmaceutical agent from each compartment to the next is an exponential function, the individual components of the experimentally measured plasma clearance curve can be identified by a process of curve peeling. The process of curve peeling or stripping can be performed manually or by means of a computer using standard pharmaceutical computer programs such as CSTRIP and NONLIN. A. J. Stedman and J. G. Wagner, Journal of Pharmaceutical Sciences, Vol. 65, No. 7, July 1976, pp. 1006–1010; C. M. Metzler, G. L. Elfing and A. J. McEwen, Biometrics, Vol. 30, No. 3, September 1974.

The terminal slope of the clearance curve represents the liver component after equilibration in all the compartments, if the liver is the only ultimate exit from the first compartment (plasma being part of the first volume). By the process of curve stripping, the other exponential functions can be identified. This is done by manually extrapolating the terminal linear portion back to the ordinate and subtracting this extrapolated line from the original curve to obtain a new set of points. A new curve or straight line most closely approximating these new points is thereby identified, again having a terminal linear portion that defines another slope corresponding to a second compartment of distribution. This process of curve stripping is continued until arriving at a final exponential function, that is, until the points obtained as the difference between a curve and its extrapolated terminal linear portion are most closely approximated by a straight line. The number of exponential functions defines the number of individual compartments or volumes of distribution, and their sum defines the total plasma clearance curve. In the alternative this operation can be performed using a computer with available computer programs.

A two-compartment model predicts that a plot of the logarithm of radiopharmaceutical activity in either compartment (in the case of liver function, (1) in the plasma or whole blood or (2) in the hepatobiliary system) versus time after administration is represented by the sum of two exponential functions. Fitting the sums of the exponential functions to plots of the logarithm of observed radiopharmaceutical activity in a compartment versus time permits the determination of transfer constants and compartmental values. Deviation of such constants and values, and hence of the measured clearance curves, from corresponding constants, values and clearance curves, respectively, for a normally functioning liver permits diagnosis of liver ailments. If such a semi-quantitative analysis of the clearance through the liver can be made, the radiopharmaceutical agent can be used not only to externally image the liver put also to assess liver function.

The conventional radiopharmaceutical agent for external imaging of the liver and assessment of liver function is a complex of rose bengal withe the radionuclide iodine-131. The $^{131}$I-rose bengal complex is particularly well suited for this purpose because it is excreted through the liver exclusively, not through the kidneys or through both the liver and the kidneys. Due to its exceptionally high liver specificity, $^{131}$I-rose bengal appears to follow the two-compartment model for organ function assessment radiopharmaceutical agents. After intravenous injection, $^{131}$I-rose bengal is cleared from the blood, localized in the hepatocytes and excreted into the bile enroute to the bowel. The clearance from the blood is by active transport across the polygonal cell membranes, followed by excretion first into the biliary passages and ultimately into the gastrointestinal tract. There is no significant reabsorption of $^{131}$I-rose bengal from the gastrointestinal tract in normal subjects.

However, $^{131}$I-rose bengal suffers the disadvantage of containing the iodine-131 radionuclide which emits gamma rays having the relatively high energy of 0.364 MeV, thereby imposing a relatively low limit on the maximum permissible administration dosage of $^{131}$I-rose bengal. Further the 8 day half life of the iodine-131 radionuclide results in an excessive residual radiation dose following administration of millicurie quantities of $^{131}$I-rose bengal and performance of the test. This residual radiation is a disadvantage per se and also necessitates that successive radiopharmaceutical tests be spaced by a sufficient number of days after administration of $^{131}$I-rose bengal to permit the background radiation to decay to a sufficiently low level. In addition, in cases of decreased hepatic uptake due to disease, the long half life of iodine-131 creates a problem of measuring the radioactivity level of $^{131}$I-rose bengal itself in the liver against a high radiation background of $^{131}$I-rose bengal remaining in the blood.

The radionuclides technetium-99m, cobalt-57, gallium-67, gallium-68, indium-111 and indium-113m have shorter half lives or emit lower energy gamma rays than iodine-131 and would be preferred in complexes with rose bengal. However rose bengal does not complex satisfactorily with such radionuclides.

Loberg et al., U.S. Pat. No. 4,017,596 disclose that chelates of the radiometals technetium-99m, cobalt-57, gallium-67, gallium-68, indium-111 or indium-113m with a substituted iminodiacetic acid serve as useful radiopharmaceutical imaging agents for liver. The chelating agent is preferably of the formula

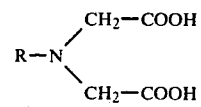

wherein R may be alkyl of up to about 24 carbon atoms, preferably about 14 carbon atoms, alkenyl, aryl alkyl or cycloaliphatic groups, substituted with halogen, hydroxy, carboxy, nitro, amino, keto or heterocyclic groups, each of which may be substituted by ether or thio-ether linkages. Additional chelating agents disclosed are compounds wherein R is combined with each methylene group to form a heterocyclic ring.

However, the Loberg et al. patent does not disclose that any member of the broad class of substituted iminodiacetic acid chelates disclosed therein is sufficiently specific to the liver as to be excreted solely by the liver. In fact, Loberg et al. indicate that chelates within the general class disclosed are cleared through either the kidneys or the liver. A chelate which is excreted through both the kidneys and liver or is reabsorbed from the gastrointestinal tract would not fit the two compartment model. Instead such a chelate would follow a three or more compartment model, and semilog plots of the chelate's experimentally measured radiopharmaceutical activity in the liver versus time could not be analyzed and quantified to assess liver function as simply as can similar plots for a chelate following a two compartment model.

SUMMARY OF THE INVENTION

It is therefore a general object of the present invention to provide a radiopharmaceutical agent which meets the aforementioned requirements and solves the aforementioned problems.

More particularly, it is an object of this invention to provide a radiopharmaceutical agent which emits gamma rays of a simple spectrum and with an energy sufficiently low to permit effective collimation and efficient detection and with a half-life sufficiently short to permit the administration of millicurie quantities to a patient without an excessive post-test background radiation and which is sufficiently stable in vivo to permit effective imaging.

Another object is to provide a radiopharmaceutical agent having a high degree of liver specificity.

Similarly an object of the present invention is to provide a method of externally monitoring the liver, which includes the intravenous administration of a solution containing the highly liver-selective radiopharmaceutical diagnostic agent of this invention.

Other objects and advantages of this invention will become apparent upon reading the following detailed description and appended claims and upon reference to the accompanying drawings.

These objects are achieved by the present invention which comprises a chelate of technetium-99m, cobalt-57, gallium-67, gallium-68, indium-111 or indium-113m and a chelating agent of formula I or a pharmaceutically acceptable metal salt thereof.

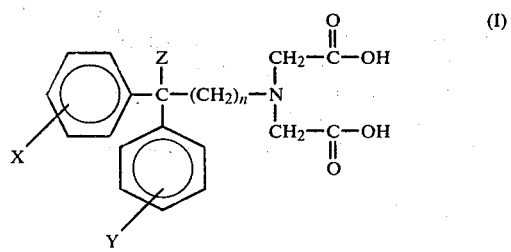

In formula I, X and Y may be the same or different and each represents hydrogen or halogen; Z represents carbamoyl or cyano, and n is an integer from 2 to 4. The present invention also comprises a method of externally monitoring the liver which includes intravenously administering a solution containing a chelate of this invention as a radiopharmaceutical agent and monitoring the distribution of the chelate in the body of the patient.

BRIEF DESCRIPTION OF THE DRAWINGS

For a more complete understanding of the invention, reference should now be made to the embodiments described below by way of examples of the invention and to the experimental results illustrated in the accompanying drawings and described below.

FIG. 3 is a semilog plot B of the measured radioactivity of a chelate of technetium-99 m/tin and N-(3-cyano-3,3-diphenylpropyl)-iminodiacetic acid per milliliter of whole blood of a dog versus the time after intravenous administration of the chelate to the dog.

DETAILED DESCRIPTION

Figure 1:
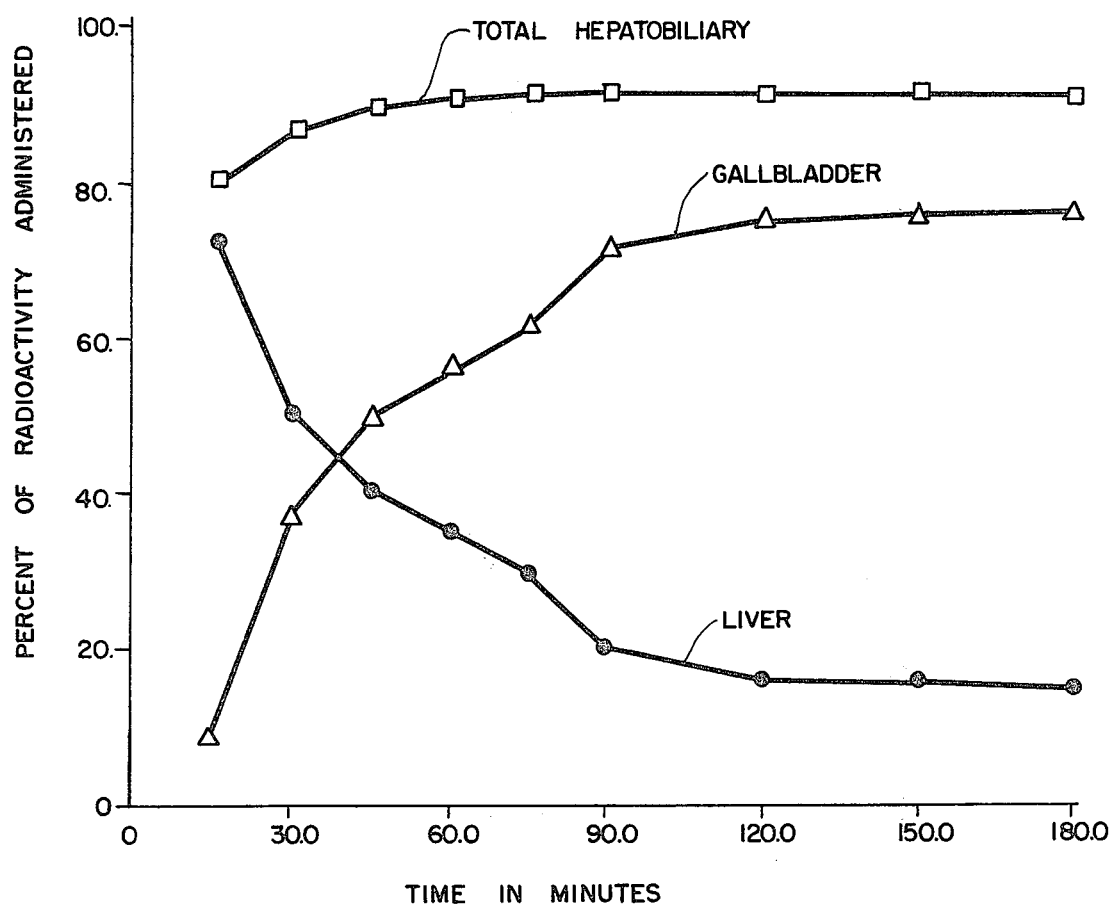
FIG. 1 contains plots of measured radioactivity found in the liver and gallbladder and in the total hepatobiliary system of a dog as a percentage of total radioactivity of a chelate of technetium-99 m/tin and N-(3-cyano-3,3-diphenylpropyl)-iminodiacetic acid administered intravenously to the dog versus time after administration.

The present invention is a chelate of technetium-99 m, cobalt-57, gallium-67, gallium-68, indium-111 or indium-113 m and a chelating agent having formula I or a pharmaceutically acceptable metal salt of such chelate.

The present invention is also a method for externally monitoring the liver and comprising administering intravenously a solution containing the aforesaid chelate and externally monitoring radiochemically its passage through the hepatobiliary system.

Suitable chelating agents include
N-(3-cyano-3,3-diphenylpropyl)-iminodiacetic acid,
N-(4-cyano-4,4-diphenylbutyl)-iminodiacetic acid,
N-(5-cyano-5,5-diphenylpentyl)-iminodiacetic acid,
N-(3-carbamoyl-3,3-diphenylpropyl)-iminodiacetic acid,
N-(4-carbamoyl-4,4-diphenylbutyl)-iminodiacetic acid,
N-(5-carbamoyl-5,5-diphenylpentyl)-iminodiacetic acid,
as well as derivatives of each in which at least one of the phenyl rings is monofluorinated, monochlorinated or monobrominated. When the chelating agent is a metal salt, the metal is suitably an alkali metal such as lithium, sodium, potassium, rubidium or cesium.

In preferred embodiments of the chelate and method of the present invention, a chelate of technetium-99 m is employed. X and Y in formula I are also preferably hydrogen. Z preferably is a cyano radical. Preferably n is 2. In more preferred embodiments of the present chelate and method, the chelating agent is N-(3-cyano-3,3-diphenylpropyl)-iminodiacetic acid. When the chelating agent is a metal salt, the metal is preferably sodium. In the most preferred embodiment of the present invention the composition is, and the method employs, a chelate of technetium-99 m and N-(3-cyano-3,3-diphenylpropyl)-iminodiacetic acid.

The chelates of the present invention can be prepared by any suitable known method from known starting materials. A particularly suitable two-step method involves as the first-step the condensation of a diester of iminodiacetic acid of formula II with a reactant of formula III to form a diester of formula IV.

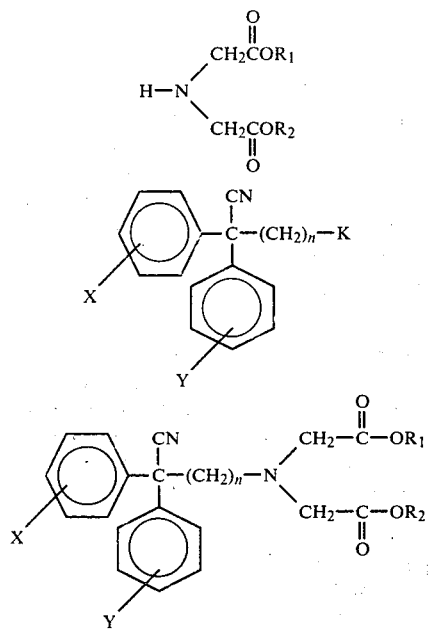

In formulas II, III and IV, X, Y, and n are as defined in formula I; K is halogen; and $R_1$ and $R_2$ may be the same or different and each represents alkyl of 1 to 5 carbon atoms. The diester of formula IV is then hydrolyzed in a second step to form the diacid of formula I wherein Z is cyano. This material can then be hydrolyzed in acidic solution to form the corresponding compound of formula I wherein Z is carbamoyl.

The chelates of this invention can then be prepared by any suitable conventional method from the aforementioned radionuclides and chelating agents of formula I. It is preferred to admix the required amount of radionuclide and the appropriate amount of chelating agent, either in the form of the acid or salt, in aqueous solution at a pH of from about 2 to 7 and then adjusting the pH of the resulting solution to about 5 to 8 either with dilute sodium hydroxide or dilute hydrochloric acid as required. If cobalt-57, gallium-67, gallium-68, indium-111 or indium-113 m are to be used, such radionuclides are readily available in forms which are suitable for direct complexation with the chelating agent. If technetium-99 m is to be used as the radionuclide, technetium-99 m is commercially available either from an isotope generator as a daughter of molybdenum-99 or as a direct product from a commercial supplier. It is also available as a solvent extraction product from molybdenum-99 solutions generally as alkaline metal pertechnetate solutions at 5–100 millicuries per milliliter. A further discussion of preparative methods therefor appears in U.S. Pat. Nos. 3,468,808 and 3,382,152.

Preferably, the radionuclide employed is technetium-99 m, and the technetium-99 m chelate is prepared by reducing a solution of a pertechnetate, for example, an alkali metal pertechnetate, in the presence of a chelating agent. The pertechnetate reducton is effected utilizing any suitable reducing agent, including stannous chloride or other stannous salts such as stannous acetate, stannous tartrate or stannous oxalate, as well as cuprous salts or ferrous salts. As a result of this reduction step, the product may contain a significant proportion of a chelate of the metal of the reducing agent, for example, the tin chelate. It is to be understood that the present invention includes the product mixture containing both the chelate of the radionuclide and the chelate of the metal of the reducing agent.

The composition of this invention is most conveniently provided as a sterile kit consisting of non-radioactive chemicals for mixing with a radiometal source prior to use. The kit may contain the chelating agent in dry form or a solution of the chelating agent, as well as a pH buffer solution, or a combination thereof, and, if technetium-99 m is to be the radiometal, a solution of a suitable reducing agent. Using sterile reagents and aseptic techniques, the respective solutions ca be mixed with each other and then with the radiometal source solution. The particular order of mixing is not critical. For example, a stannous salt solution can be added to the pertechnetate solution and the mixture combined with a solution of the chelating agent. Alternatively, a solution of the chelating agent can be combined with the pertechnetate solution prior to the addition of the stannous salt or it could be combined with the stannous salt and admixed with the pertechnetate. The resulting solution containing radiometal chelate, excess chelating agent and, if technetium-99 m is employed and if a reduction step is involved, a chelate of the metal of the reducing agent, may then be employed directly.

The utility of the chelates of this invention as radiopharmaceutical agents is evident from the following test procedures.

A volume of a solution of the chelate of technetium-99 m and N-(3-cyano-3,3-diphenylpropyl)-iminodiacetic acid prepared as in Examples 1 and 2 in the range of 0.1 to 1.0 milliliter and having a radioactivity of 1.2 millicuries and containing 0.5 to 5 milligrams of the chelate was administered intravenously to an anesthetized New Zealand rabbit weighing about 3 kilograms using a 1 milliliter tuberculin syringe connected to a #23 gauge indwelling cannula inserted into a marginal ear vein. The rabbit was positioned in a full ventral position for four hours during which time the disposition of the radioactivity in the rabbit in this position was monitored using a computer-augmented Anger camera. The measurements and results are discussed hereinafter, and the results are presented in Table 1.

This procedure used with the rabbit was repeated with additional anesthetized animals; a female beagle dog weighing 9.25 kilograms, and a female rhesus monkey weighing 7.9 kilograms. Again 0.1 to 1.0 milliliter of the solution containing 0.5 to 5 milligrams of the same chelate and prepared as in Examples 1 and 2 was administered in each case. One difference was that unlike the case of the rabbit, the chelate solution was injected intravenously in the saphenous vein of the dog or monkey. In separate tests with the female beagle, (1) a solution having 1.13 mCi of the chelate and (2) a solution having a 3.10 mCi of the chelate were administered, and the disposition of radioactivity in the dog was monitored for one hour and 3 hours, respectively. Results of these tests (1) and (2) using the female beagle dog are presented in Tables 2 and 3, respectively. In addition, FIG. 1 represents results of the test involving administration of 3.10 mCi of radioactive chelate to the female beagle dog.

TABLE 1

| Minutes After Administration | Relative Distribution of Chelate | | | |
| --- | --- | --- | --- | --- |
| | Vascular | Liver | Gallbladder | Intestine |
| 0.5 | ++ | +++ | − | − |
| 3 | − | +++ | + | + |
| 10 | − | ++ | ++ | ++ |
| 20 | − | + | ++ | +++ |
| 30 | − | + | ++ | +++ |
| 60 | − | ± | + | +++ |
| 120 | − | − | + | +++ |
| 180 | − | − | + | +++ |
| 240 | − | − | + | +++ |

TABLE 2

| Minutes After Administration | Relative Distribution of Chelate | | |
| --- | --- | --- | --- |
| | Vascular | Liver | Gallbladder |
| 1 | ++ | ++ | − |
| 10 | − | +++ | + |
| 20 | − | ++ | ++ |
| 30 | − | + | +++ |
| 40 | − | + | +++ |
| 50 | − | + | +++ |
| 60 | − | + | +++ |

TABLE 3

| Minutes After Administration | Relative Distribution of Chelate | | |
| --- | --- | --- | --- |
| | Vascular | Liver | Gallbladder |
| 10 | + | +++ | − |
| 25 | − | +++ | + |
| 35 | − | ++ | ++ |
| 65 | − | + | +++ |
| 102 | − | ± | +++ |
| 160 | − | − | +++ |

In the test using the female rhesus monkey, 0.1 to 1.0 milliliter of a solution of the chelate of technetium-99 m and N-(3-cyano-3,3-diphenylpropyl)-iminodiacetic acid prepared as in Examples 1 and 2 and having a radioactivity of 1.23 mCi and containing 0.5 to 5 milligrams of the same chelate was administered and the disposition of the radioactive material in the monkey was monitored for one hour. The results of measurements with the monkey are presented in Table 4.

At various times after administration of a solution of a chelate of this invention which are indicated in Tables 1-4, scintiscan photographs and video tape recordings were taken of the rabbit, female beagle and monkey using the Anger camera. This instrument was a Pho-Gamma LFOV Scintillation Camera System, Model 6413, fitted with a Model 3137 Vari-Back Camera, a Model 3122 Data-Store/Playback System and a Model 27851 Analog-Digital/Digital-Analog Converter (all Searle Radiographics, Inc.). This entire system was interfaced with a Xerox 530 computer (Xerox Corp., Minneapolis, Minn.) which was programmed to record net counts per unit of time and percents of total counts in individual organs and to plot organ radioactivity versus time and to separate the radioactivity of the gallbladder from the radioactivity of the liver. The camera was operated with a 140 keV high resolution Type II converging collimator using a 20 percent technetium-99 m window. Generally 400,000 counts were accumulated on each scintiscan using both video tape and self-developing film, with the animal in the full ventral position. The photographs represented a visualization of the anatomic relationships in the hepatobiliary system.

TABLE 4

| Minutes After Administration | Relative Distribution of Chelate | | | |
| --- | --- | --- | --- | --- |
| | Vascular | Liver | Gallbladder | Intestine |
| 1 | + | +++ | − | − |
| 10 | − | +++ | + | + |
| 20 | − | +++ | + | ++ |
| 30 | − | ++ | + | +++ |
| 40 | − | ++ | + | +++ |
| 50 | − | + | + | +++ |
| 60 | − | + | + | +++ |

The video tape was processed by computer for quantification of the distribution of the technetium-99 m chelate radioactivity in the organs of the animals. Tables 1-4 contain semi-quantitative representations of the distribution of radioactivity in the organs of the test animals calculated from the scintiscans. In Tables 1-4, (−), (±), (+), (++) and (+++) indicate relative amounts of measured radioactivity ranging from (−) for no statistically significant measured radioactivity to (+++) for the maximum measured radioactivity.

Referring to Table 1, there was extensive distribution throughout the vascular system of the rabbit with the heart, aorta, kidneys and liver strongly radioactive within 0.5 minutes after administration of the chelate of this invention. The chelate was rapidly cleared from the circulatory system by the liver, and within 3 minutes after administration of the chelate to the rabbit, the chelate appeared in the gallbladder, and excretion of the chelate therefrom into the intestinal tract began. Within 120 minutes after administration, no measurable radioactivity appeared in the hepatic perenchyma, a relatively small amount appeared in the gallbladder, and the bulk of the chelate was in the intestine. Clearance of the chelate from the vascular system was effected solely by the liver and biliary excretion.

Turning to Tables 2-4, the distribution of the radioactive chelate in the organs of the female beagle and monkey is similar to that in the organs of the rabbit, and clearance of the vascular system in the female beagle and monkey was also effected exclusively by the liver and biliary excretion. In both the female beagle and the monkey, the appearance of the chelate in the gallbladder was slower than in the case of the rabbit. The excretion of the chelate from the gallbladder into the intestine was slower in the female beagle than either in the rabbit or monkey since dogs usually do not have a spontaneous emptying of the gallbladder.

The disappearance of the radioactive chelate from the liver and its appearance in the gallbladder of the female beagle as well as the presence of the radioactive chelate in the total hepatobiliary system of the female beagle was calculated from video tape measurements by the computer and are plotted as percentages of total radioactivity administered in the form of the radioactive chelate versus time after administration in FIG. 1. At about 120 minutes after administration, about 75 percent of the total radioactivity administered was concentrated in the gallbladder, and in excess of 90 percent of the total dose of the radioactive chelate was in the hepatobiliary system. Approximately 50 percent of the radioactive chelate in the total hepatobiliary system had passed from the liver into the gallbladder within about 45 minutes after administration.

In addition, periodically during the time of monitoring the distribution of radioactivity in the female beagle, blood samples were removed from the jugular vein of the animal and collected in vacuum tubes containing the disodium salt of ethylendiaminetetraacetic acid and the radioactivity of one milliliter samples of plasma was measured in a gamma spectrometer. The results are presented in FIG. 2.

The procedures for injecting and taking and analyzing blood samples from the female beagle were repeated with a male mongrel dog weighing 14.1 kilograms, and the results are presented in FIG. 3. In this case, a sample of 0.1 to 1.0 milliliter of a solution of the chelate of technetium-99 m and N-(3-cyano-3,3-diphenylpropyl)-iminodiacacetic acid prepared as in Examples 1 and 2 and having a radioactivity of 3.08 mCi and containing 0.5 to 5 milligrams of the chelate was administered. In this case, the radioactivity of one milliliter samples of whole blood was measured.

Figure 2:
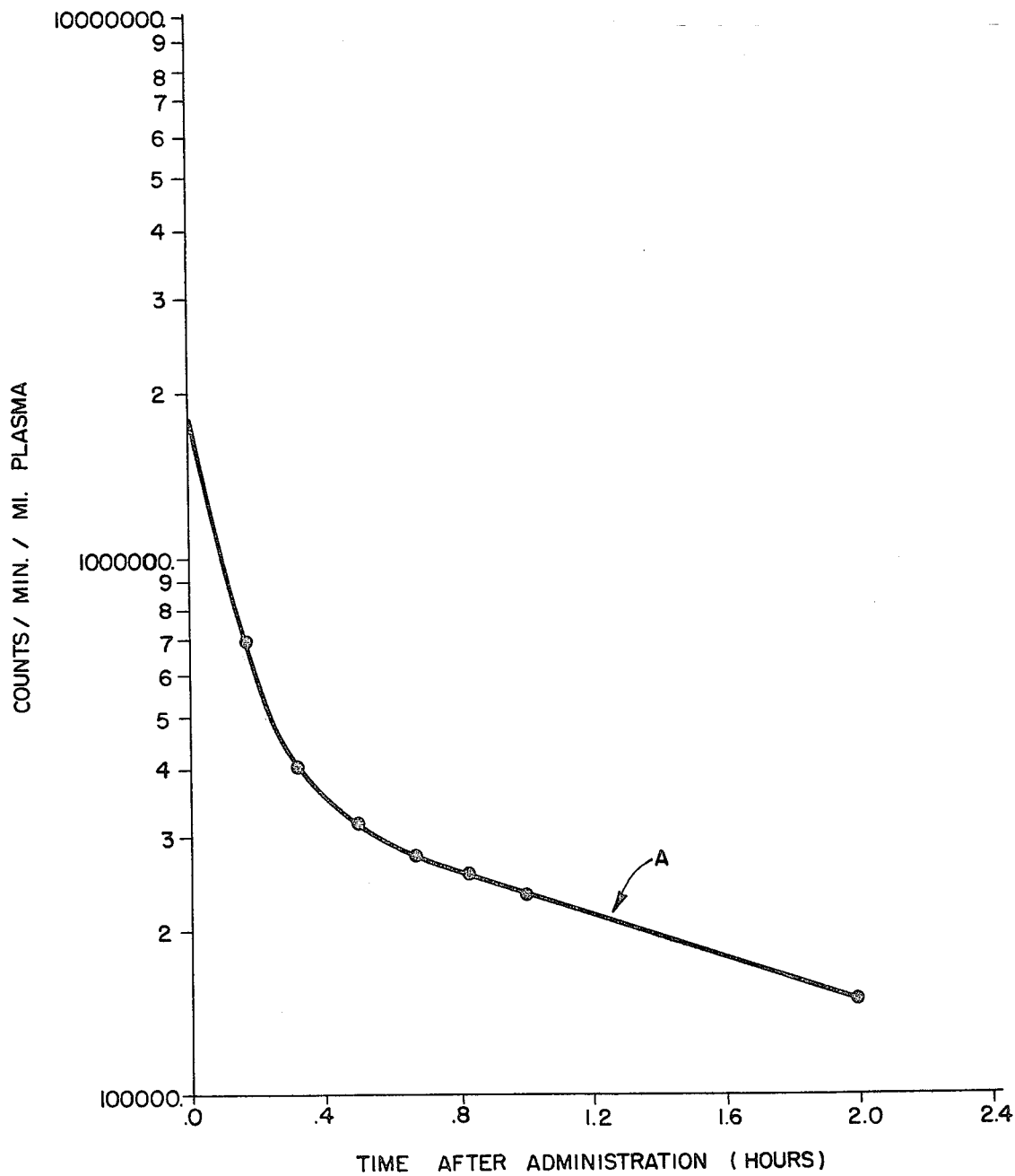
FIG. 2 is a semilog plot A of the measured radioactivity of a chelate of technetium-99 m/tin and N-(3-cyano-3,3-diphenylpropyl)-iminodiacetic acid per milliliter of plasma of a dog versus the time after intravenous administration of the chelate to the dog.

The gamma spectrometer employed was a Model 1185 Gamma Scintillation Spectrometer (Searle Analytic Inc., Des Plaines, Ill.). One milliliter samples of plasma or whole blood were analyzed for technetium-99 m, and samples were counted for 1 minute. FIGS. 2 and 3 show the radioactivity present in the plasma or whole blood, respectively, versus the time in hours after administration of the chelate to the animals. As determined by the computer, curves A and B were the best fitting curves passing through the plots of experimentally measured radioactivities. In each case, the plots of experimentally measured radioactivities were found to follow a bi-exponential decay, indicating that the clearance of the chelates of this invention, like $^{131}$I-rose bengal follow a two-compartment model for radiopharmaceutical agents. The distributive phase for the clearances shown in FIGS. 2 and 3 have half times of 0.1 and 0.13 hours, respectively. The elimination phases of the clearances shown in FIGS. 2 and 3 have half time of 1.5 hours and 3.5 hours, respectively. This illustrates that, after being distributed throughout the body the chelate of this invention is cleared relatively quickly from the liver.

During the first 3 hours after administration of a chelate of this invention to test animals, the ratios of the measured radioactivity of the liver to the measured background radiation were 10-20 to 1, while the measured radioactivity in the gallbladder to the measured background radioactivity was 150-200 to 1, permitting clear imaging, or visualization, of these organs apart from their surroundings as well as distinction of the gallbladder and and biliary tree from the initially high background of the surrounding liver tissue so that in all species the conformation of these organs was easily seen and distinguished.

Furthermore, after being administered intravenously, the chelate of this invention was rapidly distributed throughout the cardiovascular system. The liver selectively concentrated the material so that, for example, in the female dog, more than 85 percent of the administered radioactivity was accumulated in the hepatobiliary system during the first 30 minutes. The rate at which the liver cleared the chelate from the vascular system was sufficiently rapid to permit functional evaluation of hepatic tissue. In the dog more than 70 percent of the administered chelate appeared in the liver within 15 minutes after its administration, permitting this rate of movement of the chelate to be a measure of parenchymal cell concentrating functions.

With the rapid clearance of the chelate of this invention from the cardiovascular system, there was a concomitant transfer of radioactivity to the gallbladder, with virtually no urinary excretion. Measurement of the urine of the male mongrel dog revealed less than 0.5 percent of the total radioactivity administered to the dog to be in the urine through 2 hours after administration of the chelate. Monitoring the rate of excretion of the chelate from the gallbladder into the intestinal tract permits the accessment of an additional hepatobiliary function.

These results are, of course, specified merely for the purposes of illustration and, accordingly, are not to be construed as either delimiting or exclusionary. Appropriate dosages in any given instance, of course, depend upon the species of mammal involved including its size and any individual idiosyncrasies which obtain.

The present invention will be more clearly understood from the following specific examples. Throughout the examples hereinafter set forth, relative amounts of materials are given in parts by weight, unless otherwise specified.

EXAMPLE 1

Ten parts of 4-bromo-2,2-diphenyl-butyronitrile and 19 parts of diethyl iminodiacetate were mixed in 50 parts of dimethylsulfoxide solvent and heated for about 20 hours over a steam bath. The mixture was cooled to about 30° C., diluted with about 440 parts of toluene and washed each of three times with 250 parts of cold (10°-20° C.) water, to remove the dimethylsulfoxide. The resulting toluene solution was then extracted with 50 parts of one normal aqueous hydrochloric acid and washed each of three times with 50 parts of water at ambient temperature, to thereby remove unreacted diethyl iminodiacetate. The toluene solution was next dried over potassium carbonate and filtered, and the filtrate was evaporated at a temperature of 30°-50° C. and under a pressure of 10 millimeters of mercury, to yield a brown oil as a mixture containing diethyl-N-(3-cyano-3,3-diphenylpropyl) iminodiacetate. Diethyl-N-(3-cyano-3,3-diphenylpropyl)iminodiacetate was separated chromatographically from this mixture. First, impurities were removed by eluting the mixture through a silica gel column using as the eluting solvent 50 percent by volume of ethyl acetate in hexane. A yellow syrup comprising diethyl-N-(3-cyano-3,3-diphenylpropyl) iminodiacetate was separated from the resulting mixture in a second silica gel column using as the eluting solvent first 25 percent by volume of ethyl acetate in hexane and then 50 percent by volume of ethylacetate in hexane.

This syrup was dissolved at ambient temperature in about 4 parts of a 0.93 normal solution of potassium hydroxide in methanol. The solution was allowed to react for 20 hours, after which a trace of insoluble material was removed by filtration, and methanol as evaporated from the filtrate in a steam of nitrogen at ambient temperature. The residue was dissolved in water, and the solution as filtered to remove a trace of insoluble material. Free N-(3-cyano-3,3-diphenylpropyl)-iminodiacetic acid was then precipitated from the filtrate by acidification with one normal aqueous hydrochloric acid. The free N-(3-cyano-3,3-diphenylpropyl)-iminodiacetic acid was a viscous syrup which hardened slowly. The hardened product was then crushed to a powder, filtered, washed with water and dried in vacuo to a solid product. This product was recrystallized from chloroform, precipitating as a gel. The gel was filtered, washed with chloroform and dried in air, leaving a product which was powdered and dried at room temperature and under a reduced pressure of 0.07 millimeter of mercury.

EXAMPLE 2

Labeled sodium pertechnetate in normal saline solution was obtained by elution from a commercial technetium-99 m generator at a radioactivity level of 9 mCi per milliliter. Two parts of this solution were combined with 0.018 parts of the chelating agent prepared in Example 1 dissolved in 0.7 part of 0.1 normal sodium hydroxide. To this solution were added 0.025 part of an aqueous solution containing 0.036 part of stannous chloride dihydrate and 0.9 part of one normal hydrochloric acid. The pH of the resulting mixture was adjusted to 4.70 using 0.1 normal hydrochloric acid. The mixture was heated at 100° C. for 5 minutes and was then cooled to room temperature, and the pH was readjusted to 5.85 with 0.1 normal sodium hydroxide. Thin layer chromatographic analysis indicated that approximately 99 percent of the pertechnetate in the product was in the reduced form and polyacrylamide gel column chromatography indicated that approximately 87 percent of the technetium was in the form of the chelate of technetium-99 m and N-(3-cyano-3,3-diphenylpropyl)-iminodiacetic acid.

EXAMPLE 3

A mixture of 10 parts of N-[4-(4-bromophenyl)-4-cyano-4-phenylbutyl]-iminodiacetic acid, 50 parts of concentrated sulfuric acid and 10 parts of glacial acetic acid and 10 parts of water is heated overnight on a steam bath. This reaction mixture is then cooled and poured into excess ice. Solid N-[4-(4-bromophenyl)-4-carbamoyl-4-phenylbutyl]-iminodiacetic acid which precipitates is removed by filtration and recrystallized from chloroform.

EXAMPLE 4

Two parts of a solution of gallium-67 citrate in normal saline at a radioactivity level of 6 mCi per milliliter are combined with 0.015 part of N-[4-(4-bromophenyl)-4-carbamoyl-4-phenylbutyl]-iminodiacetic acid prepared in Example 3 dissolved in 0.6 part of 0.1 normal sodium hydroxide. The pH of the resulting mixture is adjusted to 4.70 using 0.1 normal hydrochloric acid. The mixture is heated at 100° C. for 5 minutes and is then cooled to room temperature, and the pH is readjusted to 5.85 with 0.1 normal sodium hydroxide. The resulting product is a chelate of gallium-67 and N-[4-(4-bromophenyl)-4-carbamoyl-4-phenylbutyl]-iminodiacetic acid.

From the above description it is apparent that the objects of the present invention have been achieved. While only certain embodiments have been set forth, alternative embodiments and various modifications, both of materials and methods, are apparent from the above description and examples to those skilled in the art. Such alternatives and modifications are considered equivalents and within the spirit and scope of the present invention.

We claim:

1. A chelate of technetium-99 m, cobalt-57, gallium-67, gallium-68, indium-111 or indium-113 m and a compound having the formula

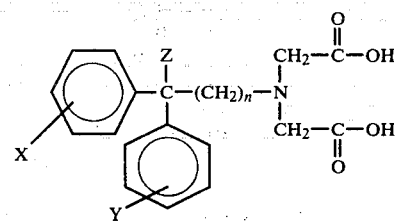

wherein X and Y can be the same or different and each represents hydrogen or halogen, Z is carbamoyl or cyano, and n is 2, 3 or 4, or a pharmaceutically acceptable metal salt thereof.

2. The chelate of claim 1 of technetium-99 m.
3. The chelate of claim 1 wherein X and Y are each hydrogen.
4. The chelate of claim 1 wherein Z is cyano.
5. The chelate of claim 1 wherein n is 2.
6. The chelate of claim 1 of N-(3-cyano-3,3-diphenylpropyl)-iminodiacetic acid.
7. The chelate of claim 1 of a sodium salt of said compound.
8. The chelate of claim 1 comprising technetium-99 m and N-(3-cyano-3,3-diphenylpropyl)-iminodiacetic acid.
9. A method of externally monitoring a mammalian liver comprising administering intravenously to the mammal a solution of a chelate of claim 1 and measuring radioraphically the distribution of the chelate throughout the body and its clearance through the liver.

* * * * *